(12) United States Patent
Wenzel et al.

(10) Patent No.: US 12,654,024 B2
(45) Date of Patent: Jun. 16, 2026

(54) DEVICE AND METHOD FOR IMPROVED INDUCTION OF NOISE BY MEANS OF ELECTROMAGNETIC RADIATION

(71) Applicant: Universitaet des Saarlandes, Saarbruecken (DE)

(72) Inventors: Gentiana Ioana Constanta Wenzel, Homburg (DE); Bernhard Schick, Hofbieber (DE); Achim Langenbucher, Saarbruecken (DE); Klaus Kruttwig, Hagen (DE); Eduard Arzt, Saarbruecken (DE)

(73) Assignee: Universitaet des Saarlandes, Saarbruecken (DE)

( * ) Notice: Subject to any disclaimer, the term of this patent is extended or adjusted under 35 U.S.C. 154(b) by 1020 days.

(21) Appl. No.: 17/776,735

(22) PCT Filed: Nov. 13, 2020

(86) PCT No.: PCT/EP2020/081986
§ 371 (c)(1),
(2) Date: May 13, 2022

(87) PCT Pub. No.: WO2021/094499
PCT Pub. Date: May 20, 2021

(65) Prior Publication Data
US 2022/0395695 A1 Dec. 15, 2022

(30) Foreign Application Priority Data
Nov. 15, 2019 (DE) ..................... 10 2019 130 958.1

(51) Int. Cl.
*A61N 5/06* (2006.01)
*H04R 25/00* (2006.01)

(52) U.S. Cl.
CPC ............. *A61N 5/06* (2013.01); *H04R 25/606* (2013.01); *A61N 2005/0605* (2013.01); *H04R 2430/20* (2013.01)

(58) Field of Classification Search
None
See application file for complete search history.

(56) References Cited

U.S. PATENT DOCUMENTS

| | | | | | |
|---|---|---|---|---|---|
| 5,925,453 | A | * | 7/1999 | Kase | ................. B32B 17/10009 428/323 |
| 6,249,587 | B1 | * | 6/2001 | Clavadetscher | ..... H04R 25/658 381/322 |

(Continued)

FOREIGN PATENT DOCUMENTS

| | | |
|---|---|---|
| EP | 3 421 019 A1 | 1/2019 |
| WO | 93/10730 A1 | 6/1993 |

(Continued)

OTHER PUBLICATIONS

Boyadzhieva et al., "A Self-Adhesive Elastomeric Wound Scaffold for Sensitive Adhesion to Tissue," Polymers, vol. 11, No. 6, May 2019, pp. 942. (pp. 15).

(Continued)

*Primary Examiner* — Yi-Shan Yang
(74) *Attorney, Agent, or Firm* — Mueting Raasch Group

(57) ABSTRACT

Provided herein is a device for improved induction of sound by electromagnetic radiation, comprising a carrier layer; a first substance having a reflective property with respect to electromagnetic radiation having a predetermined wavelength spectrum; and a second substance having an absorptive property with respect to electromagnetic radiation having said predetermined wavelength spectrum; wherein said (Continued)

Figure 1:

first substance is disposed in a region between said carrier layer and said second substance. Furthermore, a corresponding method is provided.

21 Claims, 2 Drawing Sheets

(56)                 References Cited

U.S. PATENT DOCUMENTS

| | | | |
|---|---|---|---|
| 2021/0092532 A1* | 3/2021 | Langevoort | .......... H04R 25/505 |
| 2021/0211811 A1* | 7/2021 | Fritzsche | ............. H04R 25/556 |

FOREIGN PATENT DOCUMENTS

| | | |
|---|---|---|
| WO | 2006/042298 A2 | 4/2006 |
| WO | 2010/086452 A1 | 8/2010 |
| WO | 2010/086453 A1 | 8/2010 |

OTHER PUBLICATIONS

Zhang, K.Y., et al. (2009) "Optoacoustic induced vibrations within the inner ear," Optics Express, 17:23037-23043.

* cited by examiner

Fig. 3
30
31 ⌐ first step
32 ⌐ second step
Fig. 4A
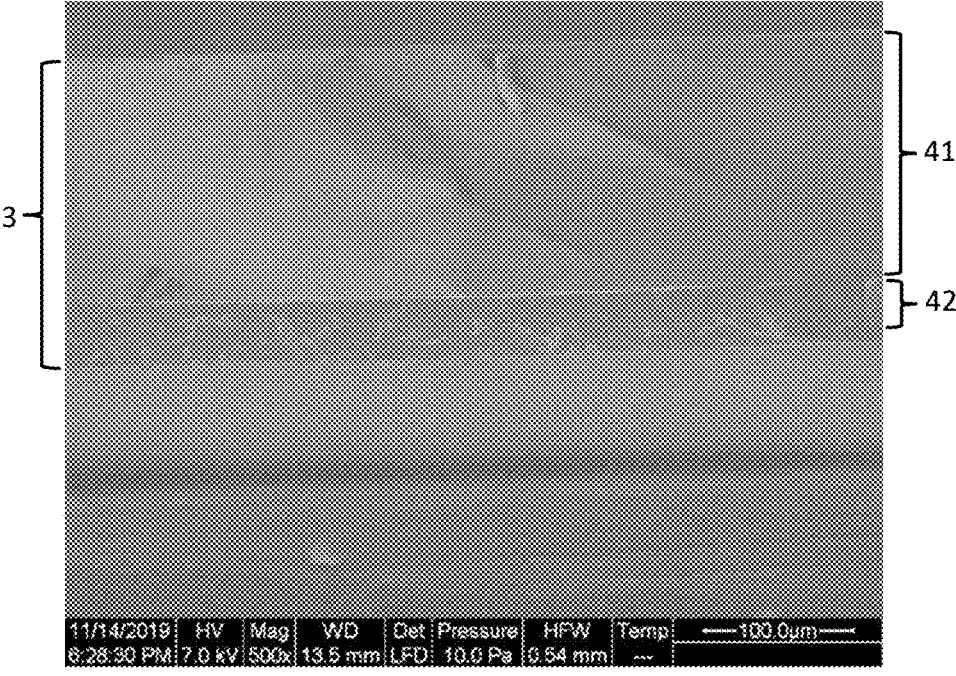
Fig. 4B
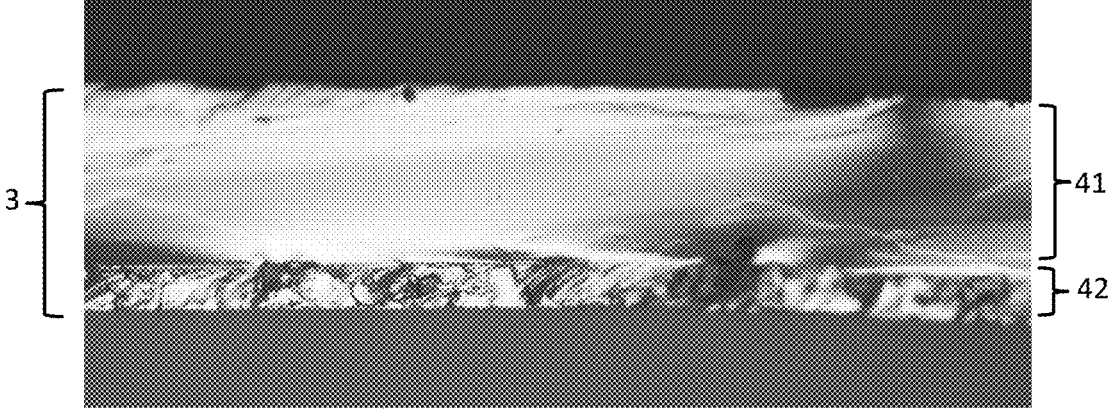

DEVICE AND METHOD FOR IMPROVED INDUCTION OF NOISE BY MEANS OF ELECTROMAGNETIC RADIATION

PRIORITY CLAIM

This application claims priority to International Application No. PCT/EP2020/081986, filed Nov. 13, 2020, which claims priority to German Application No. 10 2019 130 958.1, filed Nov. 15, 2019, wherein the contents of said applications are incorporated herein by reference in their entireties.

The care of patients with varying degrees of hearing impairment is unsatisfactory despite all further developments of conventional and implantable hearing prostheses. Especially when it comes to noise and complex acoustic signals such as music, the hearing aids available today cannot provide hearing capabilities close to the natural ones and are therefore still unsatisfactory. This inadequacy of today's hearing aids is caused, among other things, by the difficulty of the required very frequency-specific activation of the hearing system, which cannot yet be accomplished to a sufficient degree with the currently available hearing aids.

A fundamental alternative to mechanical and electrical stimulation strategies is provided by the activation of the hearing system by means of light. The distinctive feature of light as an information transmission medium is that it is a form of energy that can be applied in a very targeted and low-scattering manner. Furthermore, the intensity or wavelength of light can be modulated continuously or applied in pulsed form. In principle, an optimized activation of the hearing system can be achieved in this manner.

Targeted direct mechanical stimulation of defined sections of the inner ear using laser pulses is already known in the state of the art (e.g., "Optoacoustic induced vibrations within the inner ear"; Zhang K Y, Wenzel G I, Balster S, Lim H H, Lubatschowski H, Lenarz T, Ertmer W, Reuter G; Opt. Express, 2009 Dec. 7; 17(25):23037-43). For that purpose, a Nd:YAG laser in the green spectral range (532 nm) was used to stimulate the cochlea (the inner ear) through the round window membrane. This allowed activation of the peripheral auditory organ and derivation of corresponding electrical signals from both the brainstem and the central auditory pathway. The amplitude of the neuronal responses could be modulated in accordance with the applied pulse energy. Further investigations revealed that the application of light pulses in the middle ear and auditory canal with parameters capable of inducing an optoacoustic effect also activated the auditory organ.

Based on these first basically successful tests, various parameters of the system such as wavelength, laser pulse energy, pulse repetition frequency, pulse duration and irradiation target structure were tested for their optimal range of application with the overall goal of producing optical hearing prostheses. For the optimization and practicability of an optical hearing aid, an optimized absorption of the irradiated photons in the target structure, e.g. the eardrum, is required. The basic framework requirement is that the healthy eardrum is largely transparent and therefore absorbs only part of the applied light.

In view of the aforementioned background, the task of the invention can be seen in optimizing the mechanical excitation of a vibratable target structure in the human peripheral auditory organ, in particular the tympanic membrane, the petrous bone including the middle ear and the inner ear, by means of light.

The task is solved by the device according to the independent patent claim and the subject-matters of the subsidiary independent patent claims. Further advantageous embodiments can be found in the dependent patent claims.

The invention is based on the realization that optimization of sound transmission to a vibratable structure of the auditory organ would be advantageous for the manufacture of optical hearing aids. According to the invention, by using a device having a pigmented or suitably colored portion and a reflective portion, the energy impinging on the device can be transmitted to the biological tissue, e.g., the tympanic membrane, with maximum power and minimum losses. Moreover, by applying the device according to the invention to the biological structure during irradiation, damage to the irradiated tissue and surrounding structures can be avoided. Overall, the device according to the invention is suitable for supporting and, if necessary, amplifying the sound optically induced in the biological structure.

According to the invention, a device is provided, in particular a device for improved induction of sound by means of electromagnetic radiation, which comprises a carrier layer, a first substance or material having a reflective property with respect to electromagnetic radiation having a predetermined wavelength spectrum, and a second substance or material having an absorbent property with respect to electromagnetic radiation having the predetermined wavelength spectrum. Here, the first substance is disposed in a region between the carrier layer and the second substance. The carrier layer may comprise at least one kind of elastomers.

By applying the structure according to the invention to a vibratable tissue, in particular to the tympanic membrane, the petrous bone including the middle ear and the inner ear, an improved optoacoustic stimulation of the vibratable tissue can be achieved compared to direct irradiation of the vibratable tissue (i.e. without the device according to the invention being provided thereon). The present device is a passive structure which is devoid of electrical and electronic elements. While the second substance has a high absorptivity with respect to the wavelength(s) of electromagnetic radiation used for the optoacoustic stimulation, for example, laser radiation, the first substance has a high reflectivity with respect to the wavelength(s) of electromagnetic radiation. The first substance may be, for example, aluminum and/or silver or a mixture thereof, in particular a thin layer thereof disposed on the carrier layer. However, the reflective region of the device may also be formed by other means. The first substance may also comprise a plurality of dielectric layers forming a wavelength selective mirror (dichroic mirrors) with respect to the wavelength(s) of electromagnetic radiation. When using laser light in the optical range, the first substance may be reflective over the entire visible wavelength range or substantial portions thereof.

From the point of view of the direction of incidence of the electromagnetic radiation, the second substance is arranged spatially in front of the first substance, for example in layers. The first substance has the task of reflecting that electromagnetic radiation which has not been absorbed by the second substance and thus prevents propagation of the electromagnetic radiation through the device according to the invention. In this way, the device according to the invention simultaneously protects the vibratable tissue from the detrimental impact of the electromagnetic radiation.

The carrier layer may be a flexible backing substrate, wherein its surface facing the biological tissue being adhesive. Alternatively, an adhesive may be applied to this surface to attach the device to the biological tissue. Further, the carrier layer may be manufactured of a biocompatible material so that the device can be readily attached to the vibratable tissue. The device may be a patch that has an adhesive/sticky surface for application to the vibratable tissue. The entire device may have a thickness in the range of about 80 μm to about 2000 μm, preferably in the range of about 100 μm to about 200 μm.

The device according to the invention may be a photon-activatable structure for sound transmission, which is passive, simply structured or specifically microstructured and, when applied to the vibratable target tissue, enables support of sound transmission to the vibratable target tissue, such as the eardrum, by optical stimulation. Further, by providing the first substance on the carrier layer (although providing the first substance within the support layer is also possible) and by providing the second substance on or over the first substance, thermal isolation to the target structure can be achieved. In other words, the second substance, which is configured to optimally absorb the electromagnetic radiation, can be isolated from the vibratable target tissue at least by virtue of the transverse dimension of the carrier layer, so that a heat transfer from the second substance to the vibratable target tissue can be minimized.

The basic operation of the device according to the invention is based on the photoacoustic effect, by which acoustic excitations or waves are generated by absorption of electromagnetic energy. The absorption of electromagnetic radiation occurs primarily by means of the second substance or primarily in a layer containing the second substance. The energy input leads to a thermal expansion within the device, which results in a mechanical vibration or excitation. In other words, by means of the second substance absorbing the electromagnetic radiation, the electromagnetic (preferably optical) excitation is converted into a mechanical excitation. This is particularly the case when the time scale of the transit time of the material stress generated by heat impact through the device is greater than a pulse duration of the electromagnetic radiation incident on the device. The presence of this condition is referred to as stress confinement. When the device is provided on the tympanic membrane as an organic target structure, it may preferably be placed in an area of the tympanic membrane above the umbo to provide good mechanical excitation of the tympanic membrane.

According to further embodiments of the device, the carrier layer may have two layers adjacent to each other. Generally, the thickness of the first layer may be in the range of tens of micrometers and may be, for example, 40 μm. Generally, the thickness of the second layer may also be in the range of tens of micrometers, for example in the range of about 10 μm to about 100 μm, preferably in the range of about 40 μm to about 80 μm.

According to further embodiments of the device, the first layer of the carrier layer may comprise a silicone elastomer, preferably SSA MG 7-9800. The second layer of the carrier layer may also comprise a silicone elastomer, preferably Sylgard 184. Sylgard 184 has a high elastic content and exhibits relatively rigid behavior when it is applied to a carrier film and polymerized. SSA MG 7-9800 is characterized by a high viscous component. The first layer comprising SSA MG 7-9800 may be used to attach the device to the biological tissue, such as the eardrum.

According to further embodiments of the device, the first substance may form or be included in a first functional layer disposed on the carrier layer. Thus, the first substance may be formed as a reflective layer formed on the support layer. The first substance may be arranged as a coating on the carrier layer or on a layer comprising the second substance.

As mentioned above, the first substance may also comprise a dielectric material which is in the form of dielectric thin films and, in that manner, provide a reflective layer.

According to further embodiments of the device, the first functional layer may be disposed on the second layer of the carrier layer. The second layer of the carrier layer may in turn be disposed on the first layer of the carrier layer, which is for attachment to the vibratable fabric.

According to further embodiments of the device, the second substance may form or be included in a second functional layer disposed on the first functional layer. The device according to the invention may have a layered structure, wherein each layer (carrier layer and the functional layers) may have is individual thickness. The lateral extent of the first functional layer and the second functional layer does not have to correspond to the lateral extent of the support layer. In particular, the support layer may be larger than the functional layers disposed thereon. In particular, the second functional layer may comprise a black colored or pigmented layer that absorbs electromagnetic radiation, for example in the visible, near-ultraviolet and near-infrared range.

In further embodiments, a hearing aid is provided which comprises the device according to the invention described herein and a signal generator, which is arranged to record sound by means of at least one microphone and to emit electromagnetic radiation with the predetermined wavelength spectrum on the basis of the recorded sound. The emission of the electromagnetic radiation may be focused in the direction of the device. The electromagnetic radiation may preferably correspond to laser light and be emitted by a laser diode. Consequently, in the hearing device, electromagnetic radiation serves as an information transmission medium between the signal generator and the device.

According to the invention, the device described herein is provided for use in a method of mechanically exciting the tympanic membrane or another vibratable or vibrating structure of the skull, e.g., the petrous bone including the middle ear and inner ear, by means of electromagnetic radiation.

Furthermore, according to the invention, there is provided a use of the device described herein for mechanical excitation of the tympanic membrane or another vibratable or vibrating structure of the skull, wherein the device is mounted on the tympanic membrane or the further vibratable structure of the skull. In this case, the mechanical excitation is performed by irradiating the device with electromagnetic radiation, preferably a collimated or focused beam.

Further provided in accordance with the invention is a method of mechanically exciting the tympanic membrane or another vibratable structure of the skull by means of electromagnetic radiation, the method comprising applying the device described herein to the tympanic membrane or another vibratable structure of the skull, and irradiating the device with electromagnetic radiation having the predetermined wavelength spectrum.

In further embodiments of the method, the electromagnetic radiation may be in the form of modeled or modellable radiation. For example, the electromagnetic radiation may be in the form of an amplitude modulated field having a carrier frequency in the range of tens of kilohertz above about 20 kHz, for example 32 kHz, 50 kHz or more.

The device according to the invention can be used in animals as well as in humans to achieve optoacoustic excitation of the tympanic membrane (or the further vibratory structure of the skull). Depending on the size of the tympanic membrane, the dimension of the device as well as, for example, its weight can be adapted thereto. In general, the device according to the invention may have a round or circular shape. Its diameter can be adapted to the application and, for example, have a diameter of about 1 mm in the case of marine mice, and correspondingly about 1-15° mm larger in the case of application in humans. The device according to the invention is suitable for protecting the vibratable tissue, in particular a tympanic membrane, to which it is attached to from thermal damage, which manifests itself in drying out followed by pigmentation. In particular, drying out of the vibratable tissue can adversely change its mechanical properties, in particular weaken it, which can result in perforations. By using the device according to the invention for optoacoustic excitation of the vibratable tissue, a permanently damage-free mechanical excitation of the vibratable tissue can be carried out.

In the following, embodiments of the invention are described with reference to the accompanying drawings.

Figure 2:
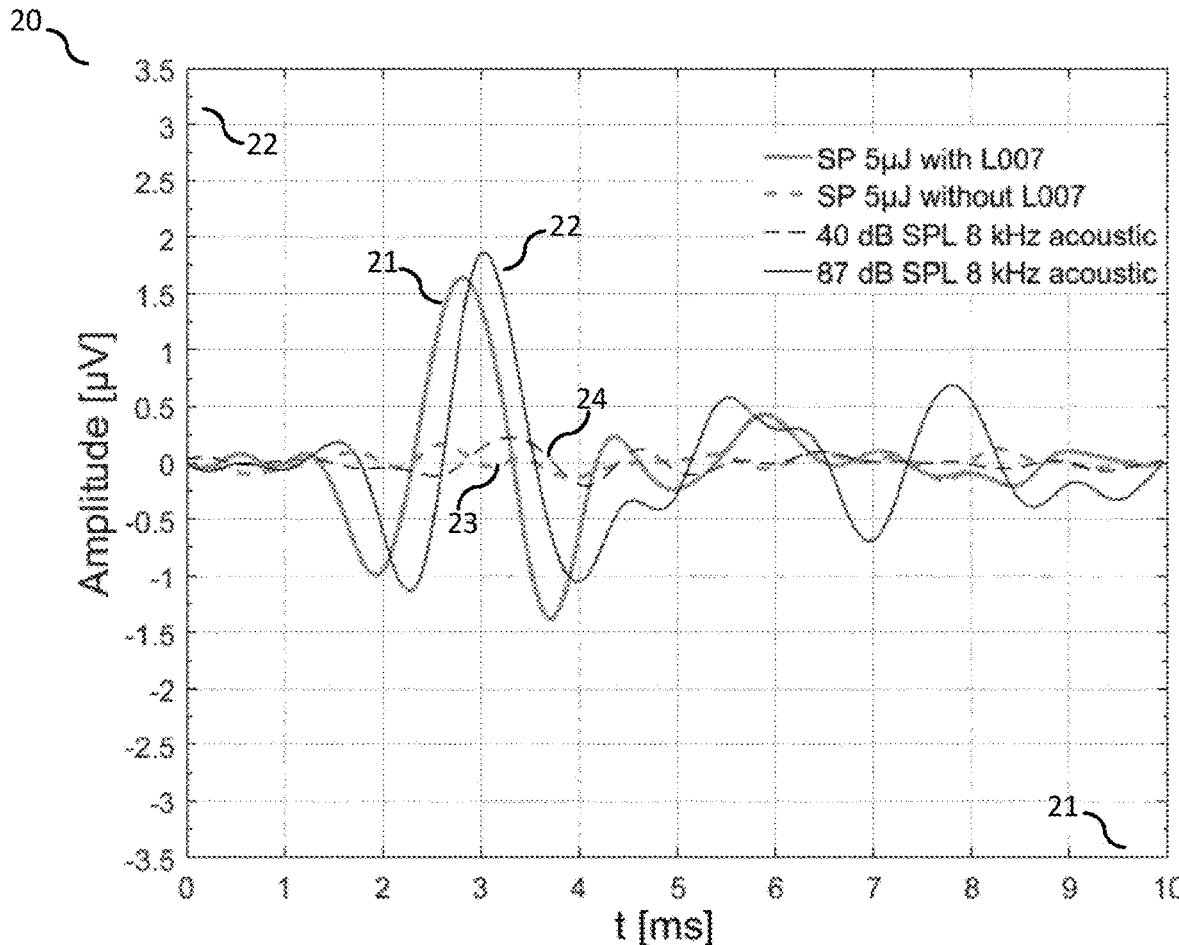

FIG. 1 shows an example of the device according to the invention,

FIG. 2 shows a diagram illustrating a comparison between acoustic and optoacoustic stimulation of the eardrum, FIG. 3 shows a flowchart illustrating an embodiment of the method according to the invention for mechanical stimulation of the tympanic membrane or another vibratory structure of the skull by means of electromagnetic radiation, FIG. 4A shows an electron microscopy image of the support layer usable for the device, and FIG. 4B shows a light microscopic image of the carrier layer usable for the device.

FIG. 1 shows an exemplary device 2 according to the invention. In the example shown, it is arranged on a tympanic membrane 1. The device 2 has a carrier layer 3. The device 2 has a first substance 4 which forms a first layer and has a reflective property with respect to electromagnetic radiation with a predetermined wavelength spectrum. Further, the device 2 comprises a second substance 5 forming a second layer having an absorbing property with respect to electromagnetic radiation having the predetermined wavelength spectrum. As shown, the first substance 4 is arranged in a region between the carrier layer 3 and the second substance 5.

An optoacoustic excitation of the tympanic membrane 1 (or, as mentioned several times, of another structure of the skull capable of vibrating) is carried out by means of electromagnetic radiation which impinges on the device 2 from the lower edge of the page. The electromagnetic radiation first impinges on the second substance 5 or the corresponding material layer, which is configured to absorb the electromagnetic radiation. That portion of the electromagnetic radiation which has not been absorbed by the first substance 5 and therefore passes through the corresponding second layer is reflected by the first substance 4 or the corresponding material layer and is prevented from penetrating the carrier layer 3 and entering the deeper tissue, e.g. middle ear. The device 2 may be attached to the eardrum 1 or to another vibratable structure of the skull by means of a glue or other adhesive.

The device 2 shown in FIG. 1 can be manufactured, for example, by first producing the carrier layer 3 from the silicone elastomers SSA MG 7-9800 and Sylgard 184. For this purpose, Sylgard 184, which has a high elastic content and exhibits relatively rigid behavior, can be applied to a carrier film and polymerized at 95° C. for 1 h. An automatic squeegee can be used to adjust the film thickness. The thickness of the polymerized film of Sylgard 184 can typically be 40 μm. MG 7-9800 can then be applied to the film of Sylgard 184 and also polymerized, and a typical film thickness can be between 40 μm and 80 μm. MG 7-9800 silicone elastomer is characterized by a high viscous component and can be used for attachment to the biological tissue, such as the tympanic membrane. Experiments have shown that multiple application and release with these layered composites is possible in mice without causing perforation of the tympanic membrane. For the formation of the device 2, the two-layer layered composite formed as described can be detached from the carrier film used for its construction. The layered composite can then be used as a carrier layer 3 and the first substance 4 and then the second substance 5 can be arranged thereon, for example in the form of corresponding layers.

By using the device according to the invention for optoacoustic excitation of a biological tissue, in particular the tympanic membrane, it is possible not only to protect it from the adverse effects of permanent irradiation with electromagnetic radiation. By using the device according to the invention, primarily in comparison with direct irradiation of the biological tissue, an increase in the amplitude of the resulting auditory activation can be achieved. This aspect is illustrated in the diagram 20 in FIG. 2, in which natural acoustic excitation has been compared with optoacoustic excitation of the tympanic membrane in an animal model (guinea pig, Charles River). On the x-axis 25 the time in milliseconds is plotted and on the y-axis 26 the measured amplitude in microvolts is plotted. A total of four graphs 21-24 are shown in the diagram. The first graph 21 represents an optoacoustic excitation of the tympanic membrane by means of an exciting optical pulse with an energy of 5 μJ when using the device according to the invention on the tympanic membrane. The second graph 22 represents a natural excitation of the eardrum with a sound pressure of 87 dB (without using the device according to the invention). The third graph 23 represents an optoacoustic excitation of the tympanic membrane by means of an excitatory optical pulse with an energy of 5 μJ without using the device according to the invention, that is, when the tympanic membrane is directly irradiated. Finally, the fourth graph 24 represents a natural excitation of the eardrum with a sound pressure of 40 dB (without using the device according to the invention).

By comparing the first graph 21 with the third graph 23, it can be seen that by using the device according to the invention, a considerable increase in the excitation amplitude in the peripheral auditory system can be achieved with a constant excitation pulse. The difference in amplitude caused by using the device according to the invention is approximately equivalent to the difference between a natural excitation of the auditory system with a sound pressure of 40 dB (fourth graph 24) and 87 dB (second graph 22). Thus, the increase in oABR (optically-evoked auditory brainstem response) amplitude achievable by using the device according to the invention is significant. In particular, the use of the device enables an optoacoustic excitation of the auditory pathway which is comparable to a natural excitation with a sound pressure level above 80 dB sound pressure.

FIG. 3 shows a flowchart 30 illustrating an embodiment of the method according to the invention for mechanical excitation of the eardrum or another vibratable structure of the skull by means of electromagnetic radiation. In a first step 31, the method comprises applying the device according to the invention to the eardrum or the further vibratable structure of the skull. In a further step 32, the method comprises irradiating the device with electromagnetic radiation having the predetermined wavelength spectrum.

FIG. 4A shows an electron microscopy image of an embodiment of the carrier layer 3, which can be used for the construction of the device according to the invention. The carrier layer 3 has a two-layer structure, with a first layer 41 comprising the silicone elastomer SSA MG 7-9800 and the second layer 42 comprising the silicone elastomer Sylgard 184. In the example shown, the first layer 41 has a thickness of 158 μm and the second layer 42 has a thickness of 42 μm. The carrier layer 3 can be produced, for example, by means of spin coating, whereby the thicknesses of the individual layers can be adjusted according to need.

FIG. 4B shows an optical microscopy image of the carrier layer 3 shown in FIG. 4A.

After completion of the carrier layer 3, the first substance can be applied to the surface of the second layer 42. For this purpose, for example, a metallic mirror layer can be vapor-deposited. Subsequently, the second substance can be applied, for example a dye/lacquer by means of a spraying process.

The invention claimed is:

1. A vibratable auditory device, comprising:
  a carrier layer;
  a first substance having a reflective property with respect to electromagnetic radiation having a predetermined wavelength spectrum;
  a second substance having an absorbing property with respect to the electromagnetic radiation having the predetermined wavelength spectrum;
  wherein the first substance is disposed in a region between the carrier layer and the second substance.

2. The device according to claim 1, wherein said carrier layer comprises two abutting layers.

3. The device according to claim 2, wherein the first layer comprises a silicone elastomer, and the second layer comprises a silicone elastomer.

4. The device of claim 3, wherein the silicone elastomer comprised by the first layer is a first silicone elastomer that comprises SSA MG 7-9800, and the silicone elastomer comprised by the second layer is a second silicone elastomer that forms a rigid film when polymerized at 95° F.

5. The device according to claim 2, wherein the first substance forms a first functional layer disposed on the carrier layer; and wherein the first functional layer is arranged on the second layer of the carrier layer.

6. The device according to claim 1, wherein the first substance forms a first functional layer disposed on the carrier layer.

7. The device according to claim 6, wherein the second substance forms a second functional layer disposed on the first functional layer.

8. A hearing aid comprising
  the device according to claim 1; and
  a signal generator arranged to record sound by means of at least one microphone and to emit the electromagnetic radiation having the predetermined wavelength spectrum based on the recorded sound.

9. The device according to claim 8, wherein the carrier layer of the device comprises two abutting layers.

10. The device according to claim 9, wherein the first layer of the device comprises a silicone elastomer, and the second layer comprises a silicone elastomer.

11. The device according to claim 9, wherein the first substance of the device forms a first functional layer disposed on the carrier layer; and wherein the first functional layer of the device is arranged on the second layer of the carrier layer.

12. The device according to claim 11, wherein the second substance of the device forms a second functional layer disposed on the first functional layer.

13. The device according to claim 8, wherein the first substance of the device forms a first functional layer disposed on the carrier layer.

14. A method for mechanical excitation of an eardrum, comprising:
  using a vibratable auditory device to excite the eardrum, wherein the vibratable auditory device comprises
    a carrier layer;
    a first substance having a reflective property with respect to electromagnetic radiation having a predetermined wavelength spectrum;
    a second substance having an absorbing property with respect to the electromagnetic radiation having the predetermined wavelength spectrum;
    wherein the first substance is disposed in a region between the carrier layer and the second substance,
    wherein the eardrum is excited by the vibratable auditory device via the electromagnetic radiation.

15. A method for mechanical excitation of a tympanic membrane or a vibratable structure of a skull other than the tympanic membrane by electromagnetic radiation, comprising:
  attaching a vibratable auditory device to the eardrum or the other vibratable structure of the skull, wherein the vibratable auditory device comprises
    a carrier layer;
    a first substance having a reflective property with respect to electromagnetic radiation having a predetermined wavelength spectrum;
    a second substance having an absorbing property with respect to the electromagnetic radiation having the predetermined wavelength spectrum;
    wherein the first substance is disposed in a region between the carrier layer and the second substance;
  irradiating the device with the electromagnetic radiation having the predetermined wavelength spectrum.

16. The method according to claim 15, wherein the carrier layer of the device comprises two abutting layers.

17. The method according to claim 16, wherein the first layer of the device comprises a silicone elastomer, and the second layer of the device comprises a silicone elastomer.

18. The method according to claim 17, wherein the silicone elastomer comprised by the first layer is a first silicone elastomer that comprises SSA MG 7-9800, and the silicone elastomer comprised by the second layer is a second silicone elastomer that forms a rigid film when polymerized at 95° F.

19. The method according to claim 16, wherein the first substance of the device forms a first functional layer disposed on the carrier layer; and wherein the first functional layer is arranged on the second layer of the carrier layer.

20. The method according to claim 19, wherein the second substance of the device forms a second functional layer disposed on the first functional layer.

21. The method according to claim 15, wherein the first substance of the device forms a first functional layer disposed on the carrier layer.

* * * * *